United States Patent [19]
Friedman

[11] 4,060,077
[45] Nov. 29, 1977

[54] RESPIRATOR

[75] Inventor: Irving Friedman, New Haven, Conn.

[73] Assignee: Diana W. Friedman, New Haven, Conn.

[21] Appl. No.: 631,374

[22] Filed: Nov. 12, 1975

[51] Int. Cl.² .......................................... A61M 16/00
[52] U.S. Cl. ................................................ 128/145.8
[58] Field of Search .............. 128/145.8, 145.6, 145.7, 128/145.5, 142, 2.08, DIG. 29, DIG. 17, 188, 202

[56] References Cited

U.S. PATENT DOCUMENTS

| | | | |
|---|---|---|---|
| 2,770,232 | 11/1956 | Falk | 128/145.8 |
| 3,420,225 | 1/1969 | Holden et al. | 128/2.08 |
| 3,808,706 | 5/1974 | Mosley et al. | 128/2.08 |
| 3,840,006 | 10/1974 | Buck et al. | 128/145.8 |
| 3,889,660 | 6/1975 | Kitrilakis | 128/2.08 |
| 3,889,672 | 6/1975 | Woldring | 128/2.08 |

FOREIGN PATENT DOCUMENTS

| | | | |
|---|---|---|---|
| 1,008,520 | 10/1965 | United Kingdom | 128/145.6 |

*Primary Examiner*—John D. Yasko
*Assistant Examiner*—Henry J. Recla
*Attorney, Agent, or Firm*—DeLio and Montgomery

[57] ABSTRACT

A respirator for infants wherein air is delivered to a nasal catheter at a preset pressure during the inspiratory phase, the flow being maintained in an amount sufficient to maintain the pressure regardless of leakage, while pressure and volume are monitored during the expiratory phase through a bellows which operates a recording device and can be adjusted to maintain a desired minimum terminal pressure at the end of the expiration; also the method of effecting respiration by means of such a respirator or equivalent devices.

9 Claims, 6 Drawing Figures

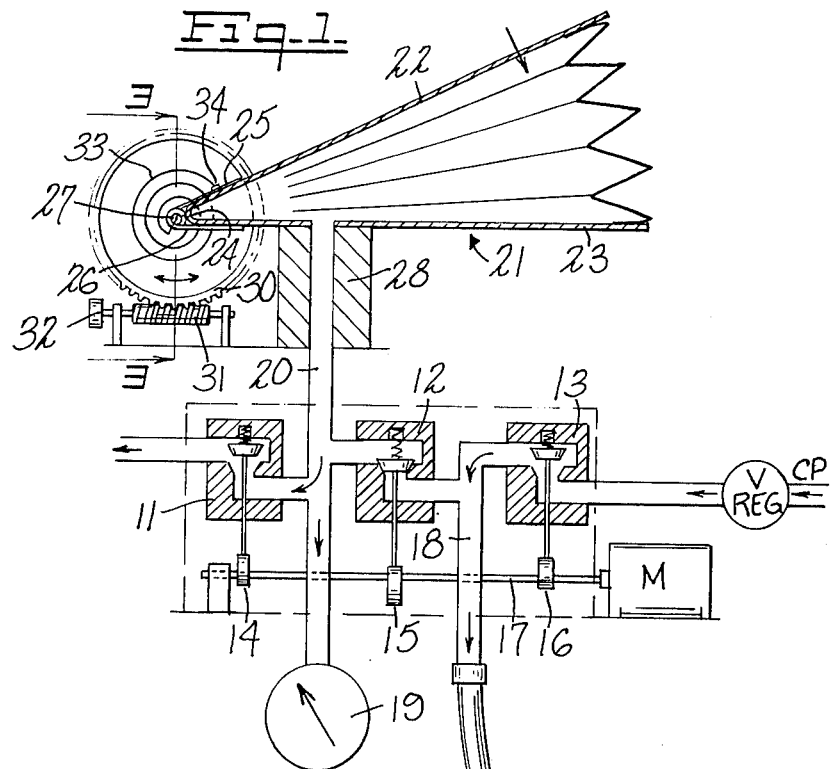
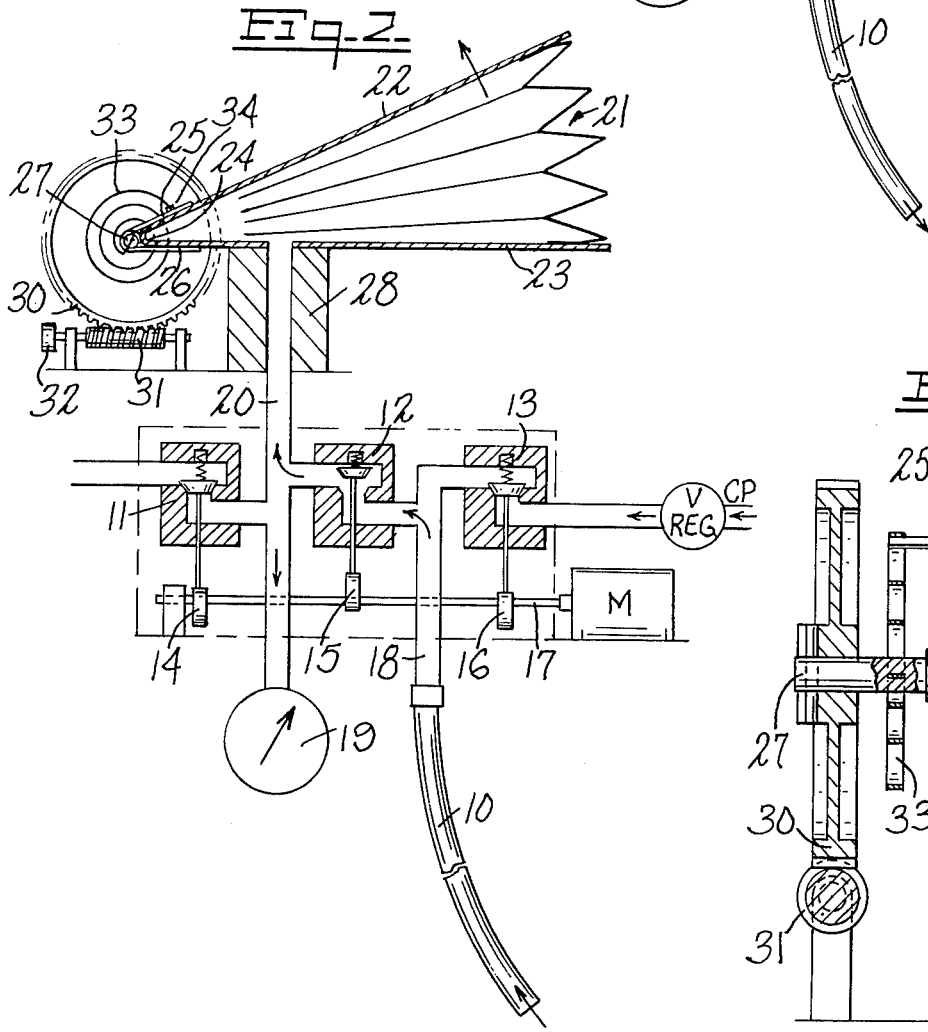
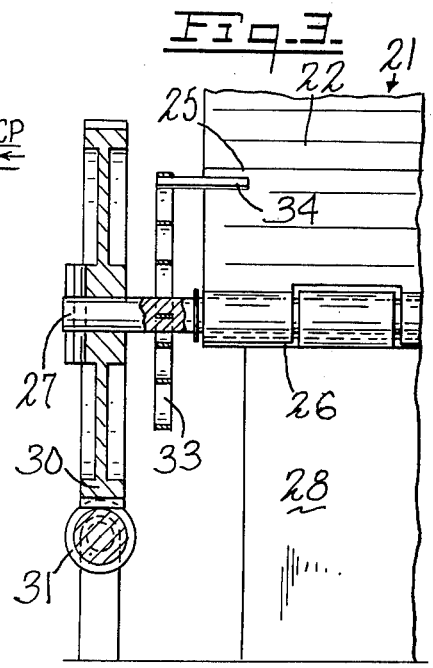

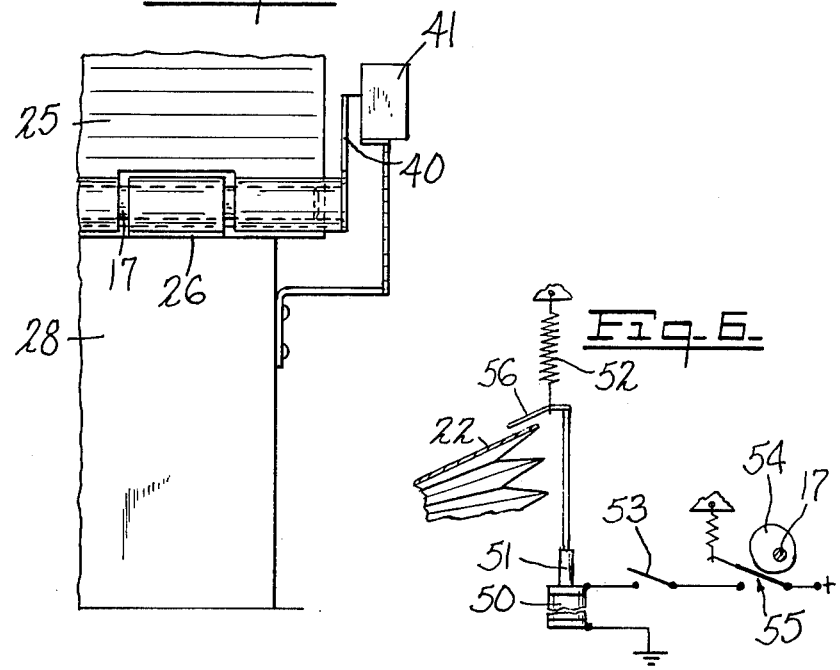
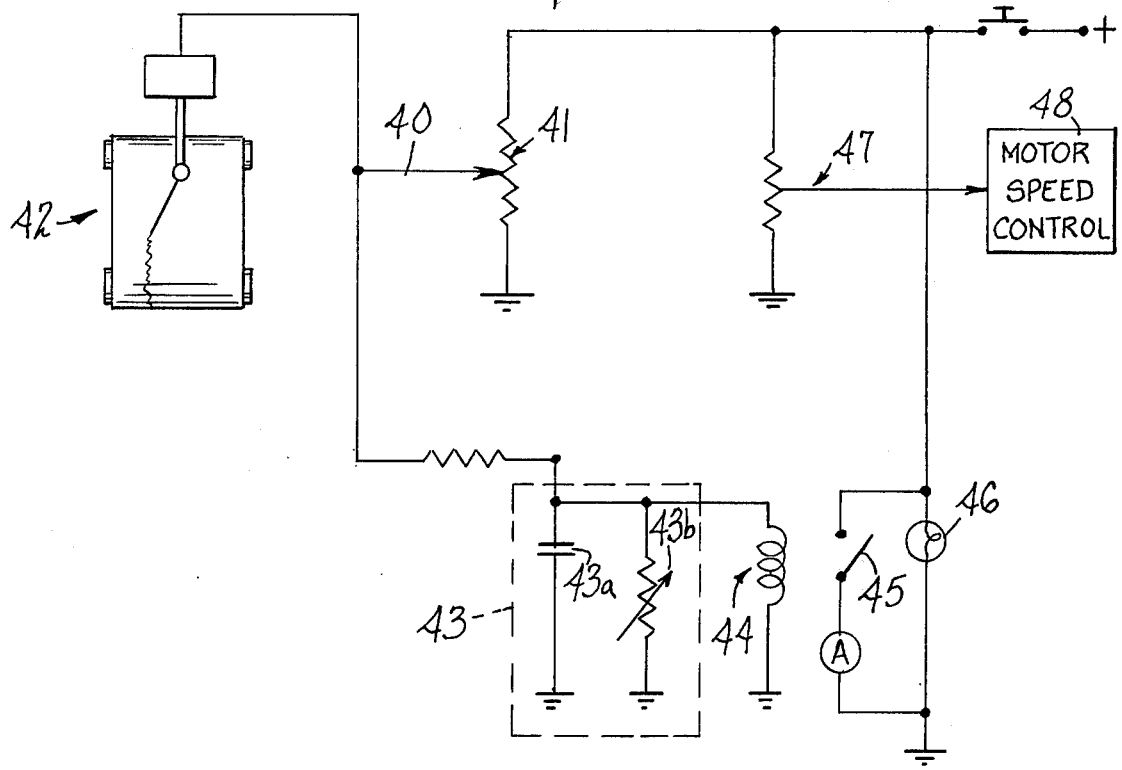

RESPIRATOR

This invention relates to a respirator for infants adapted to deliver air at a predetermined pressure during the inspiratory phase, together with means for monitoring the pressure and volume during the expiratory phase and for maintaining a desired minimum pressure at the end of the expiration; also the method of effecting respiration in the manner disclosed.

In known respirators, including those designed for use by infants, it is customary to introduce measured volumes of air into a nasal catheter, with the disadvantage that, in case of leakage at unpredictable rates around the catheter, the volume delivered to the infant's lungs may be reduced by a significant amount which is difficult to ascertain, since there is no reliable way to measure such leakage. The resulting undetected reduced ventilation may have dangerous consequences. Moreover, any changes in the infant's lung volume may escape detection.

According to the present invention, air is delivered to the nasal catheter at a pre-selected pressure which is maintained by automatic adjustment of the supply rate to compensate for leakage around the catheter as well as to avoid the possibility of excessive pressure in the event of a change in the lung capacity and/or in the rate of leakage. The volume of the respired air, i.e., that which has actually been used in the lung, is measured in the expiratory phase by means of a bellows which is filled at each expiration to an ascertainable volume at an adjustable minimum pressure which is programmed to empty itself during the inspiratory phase. There is less leakage of air around the nasal catheter in the expiratory phase since the pressure gradient is less; furthermore, leakage at this phase could only result in a slight underestimate of the respiratory volume, which might cause unnecessary concern but not dangerous complacency. The rate of supply may be determined as a function of the expiratory volume and variations therein, and the respiratory rate is controlled by the speed at which the respirator is operated.

It is an object of the invention to provide a respirator wherein the infant's respiration is monitored as a function of the volume of air expired in each respiratory cycle.

It is a further object of the invention to provide a respirator wherein air is delivered in a manner to assure the provision of an adequate supply regardless of the rate of leakage.

It is a further object of the invention to provide a respirator wherein changes in the infant's lung volume are quickly revealed without subjecting the lungs to undesirable pressure.

It is another object of the invention to provide a respirator wherein the volume measuring means functions also to maintain an adjustable minimum intrapulmonary pressure at the end of expiration, to prevent alveolar collapse.

It is a still further object of the invention to provide an improved method of effecting respiration.

It is yet another object of the invention to provide certain improvements in the form, construction and arrangement of the several parts, and in the steps of the method, whereby the above named and other objects may effectively be attained.

The invention accordingly comprises the several steps and the relation of one or more of such steps with respect to each of the others, and the apparatus embodying features of construction, combination of elements and arrangement of parts which are adapted to effect such steps, all as exemplified in the following detailed disclosure, and the scope of the invention will be indicated in the claims.

A practical embodiment of the invention is shown in the accompanying drawings wherein:

FIG. 1 represents, somewhat diagrammatically, a vertical section through the apparatus during the inspiratory phase;

FIG. 2 represents a similar section during the expiratory phase;

FIG. 3 represents a detail section on the line 3—3 of FIG. 1;

FIG. 4 represents a detail elevation showing the corner of the bellows opposite to that shown in FIG. 3 including volume recording means;

FIG. 5 is a circuit diagram showing suitable volume monitoring and recording means; and FIG. 6 is a circuit diagram showing a bellows collapsing arrangement.

Referring to the drawings, the nasal catheter 10 is assumed to be inserted, in the customary manner, in the patient. A supply of gas, such as air, with or without added oxygen, at constant pressure is indicated at CP, the rate of supply being controlled manually or otherwise by means of the regulating valve V REG.

Air flow is controlled by the series of valves 11, 12 and 13 which are shown as being actuated by cams 14, 15, 16 on a cam shaft 17 driven by the variable speed motor M. The cams are so oriented that, when valves 11 and 13 are open, valve 12 is closed (FIG. 1) and vice versa (FIG. 2), and they are preferably profiled for quick operation of the respective valves. Between valves 12 and 13 the air line 18 is connected to the catheter 10. Between the valves 11 and 12 the air line is connected to a manometer 19, and by pipe 20, to the bellows 21, constituting a reservoir.

The upper and lower walls or leaves 22, 23 of the bellows are joined in an air-tight manner along the fold 24 and are mounted between the upper and lower plates 25, 26 of a hinge, which may be of the piano hinge type, with a hinge pin or shaft 27 passing through the alternating loops of the respective hinge plates. As shown, the lower leaf 23 of the bellows is fixed on a suitable support 28. One end of the shaft 27 is extended beyond the side edge of the bellows and has fixed thereon the worm wheel 30, meshing with the worm 31 which may be rotated by means of the knob 32. Also fixed to the shaft 27 is the inner end of a spiral spring 33, the outer end of which is connected at 34 to the upper plate 25 of the hinge. Alternatively, the upper hinge plate 25 may be fixed on the shaft 27, the free end of the spring being connected to the worm wheel 30, and the latter being freely rotatable on the shaft. The function of the spring 33 is to bias the upper leaf 22 of the bellows toward its closed position, i.e., to resist expansion, and the value of such bias can be varied by rotation of the worm wheel 30, as described.

At the opposite end of the hinge the upper leaf 22 is connected to the arm 40 of a potentiometer 41 which controls the monitoring, recording and alarm system exemplified in FIG. 5, primarily as a function of the volume of air received and discharged by the bellows in each full cycle. The potentiometer is connected to a slow moving strip recorder 42 which makes a visual record of the bellows functioning, for visual reference.

It is also connected to an integrating circuit 43 wherein the movement of the potentiometer arm (i.e., its amplitude) is integrated to average the expiratory volume. The integrating circuit may take any desired form using decade resistors or capacitors. The circuits 43 is shown as comprising capacitors 43a and variable resistance 43b. The time constant of the circuit is set by resistance 43b to average over five to ten cycles. The circuit 43 is connected to the relay coil 44 which is adjusted to close the switch 45 if the integrated volume signal falls below a predetermined value, the visual or audible alarm A being thus set off. A "power on" indicator is shown at 46, and power should normally be on when motor M is running. The sensitivity of the alarm relay is adjustable, in a known manner, to respond to different minimum values. The speed of motor M is variable as through a speed control potentiometer 47 and motor speed control circuit 48 to provide inspiratory and expiratory rates of 5 to 60 cyles per minute.

In operation, with the catheter 10 in proper position, the motor M is started and the valve V REG is opened to permit an empirically pre-determined rate of air flow. During the inhalation phase the air flows through valve 13, catheter 10 and into the patient's lungs (FIG. 1). As the cam shaft 17 is rotated the valves 13 and 11 are closed, valve 12 is opened and air is exhaled, as shown in FIG. 2, through valve 12 and into the bellows, inflating it. The pressure can be read at all times during this phase by reference to the manometer 19. The force of spring 33 serves to resist slightly the inflation of the bellows so as to maintain a desired minimum terminal pressure in the lungs at the end of the expiratory phase. As the cam shaft continues to rotate the valves are returned to the position of FIG. 1, permitting air to flow again into the lungs through valve 13 and catheter 10, while the bellows is emptied through valve 11. The opening and closing of the bellows actuates the potentiometer 41 such that the indicated volume of respired air is recorded on the recorder 42 where it can be observed and correction made in the rate of supply, if necessary. When a proper rate has been determined upon, further adjustments need not be made unless a change in condition is shown by the alarm system or the need for variation is clinically indicated.

While the valves 11, 12 and 13 are shown for illustration purposes, as poppet valves, it will be understood that other types of valves such as slide or sleeve valves could be used, if desired, and solenoid operation could be substituted for cam operation. The inspiratory and expiratory phases are normally of about equal duration but variation in this ratio can be effected, if desired, as by substituting cams having different profiles or other suitable means.

From the foregoing it will be appreciated that the apparatus shown provides means for observing continuously the volume of the air actually respired at every breath. If any change is noted, appropriate clinical evaluation may be made promptly at the inception of any disorder, when timely corrective action may be critically important.

When the infant is to be removed from the respirator it is desirable that the infant become accustomed to breathing without the back pressure. Means may accordingly be provided for positively collapsing the bellows during the inspiratory phase.

As shown in FIG. 6, a solenoid 50 having a retractable plunger 51 actuated the bellows closure arm 56 which is held normally by a spring 52, at or above the upper portion of the movable portion 22 of the bellows. When a master on-off switch 53 is closed, the solenoid 50 can be energized when the cam 54 on shaft 17 closes a switch 55 to close the solenoid circuit, the switch 55 being biased toward its open position and closeable only by the cam 54. In this manner the bellows is collapsed. This would occur during the inspiratory phase of the cycle, and cam 54 is so aligned and position on shaft 17. The spring 52 returns the arm 56 to its original position when the current is off.

The system disclosed can be used to advantage if other than a nasal catheter is the means of delivering air to the infant's lungs.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

What I claim is:

1. A respirator comprising, means for establishing communication with a patient's lungs, means for continuously supplying gas at a predetermined pressure, an expansible and contractible reservoir, a first conduit containing a first valve connected between said supplying means and said communication means, a second conduit containing a second valve connected between said communication means and said reservoir said second conduit including an unobstructed passageway between said reservoir and said second valve, a third conduit containing a third valve downstream from said reservoir and also connected to said second conduit between said reservoir and said second valve, said third conduit communicating with the atmosphere when said third valve is open, means associated with said reservoir for monitoring and indicating the volume of gas received therein, and valve actuating means adapted simultaneously to open the first and third valves and close the second valve during the inspiratory phase and to simultaneously open the second valve and close the first and third valves during the expiratory phase whereby during an expiratory phase said reservoir is connected to said communication means and receives the expired gas, and means associated with said reservoir to maintain a terminal pressure on gas remaining in the lungs at the end of each expiratory phase when said second valve is open.

2. A respirator according to claim 1 which includes a pressure indicating device continuously in communication with the interior of the reservoir.

3. A respirator according to claim 1 which includes adjustable means for biasing the reservoir toward a contracted condition of minimum volume.

4. A respirator according to claim 3 wherein the reservoir is a bellows having hinged upper and lower walls and the biasing means includes a spring acting on one of said walls and means for varying the force of said spring.

5. A reservoir according to claim 1 wherein the reservoir is a bellows having relative movable upper and lower walls and wherein the volume monitoring means is actuated by the relative movement of said walls.

6. A respirator according to claim 5 wherein the volume monitoring means includes a potentiometer the arm of which is movable with one of said reservoir walls.

7. The respirator of claim 1 further including means mounted to a common shaft for sequentially operating said second valve and said first and third valves.

8. The respirator of claim 7 further including a regulating valve in said first conduit between a gas supply source and said first valve for maintaining the gas supplied to said communication establishing means at said predetermined pressure.

9. The method of effecting respiration of a patient in alternating inspiratory and expiratory phases which comprises the steps of continuously supplying gas at a predetermined pressure to the patient's lungs through a conduit during the inspiratory phases, interrupting supply of said gas at the end of the inspiratory phases, collecting a continuous unobstructed flow of the gas respired through said conduit during each expiratory phase into an expansible and contractible reservoir, connecting said reservoir to said conduit during the succeeding expiratory phase biasing said reservoir to maintain a minimum terminal pressure on gas remaining in the lungs at the end of each expiratory phase, monitoring and indicating the volume of said respired gas, releasing the collected respired gas during the next inspiratory phase, and controlling the rate of supply of the gas in accordance with the indicated volume of the gas collected during the expiratory phase.

* * * * *

UNITED STATES PATENT AND TRADEMARK OFFICE
CERTIFICATE OF CORRECTION

PATENT NO. : 4,060,077
DATED : November 29, 1977
INVENTOR(S) : Irving Friedman

It is certified that error appears in the above-identified patent and that said Letters Patent are hereby corrected as shown below:

Column 3, line 5, "circuits 43" should read --circuit 43--.

Column 4, lines 17-18 of claim 1, "adapted simultaneously to" should read --adapted to simultaneously--.

Signed and Sealed this

Second Day of May 1978

[SEAL]

Attest:

RUTH C. MASON
Attesting Officer

LUTRELLE F. PARKER
Acting Commissioner of Patents and Trademarks